United States Patent [19]
Foret et al.

[11] Patent Number: 5,916,581
[45] Date of Patent: Jun. 29, 1999

[54] IODINE ANTIMICROBIAL COMPOSITIONS CONTAINING NONIONIC SURFACTANTS AND HALOGEN ANIONS

[75] Inventors: Chris Foret, Shawnee Mission, Kans.; Thomas C. Hemling, Winnebago, Mo.

[73] Assignee: West Agro, Inc., Kansas City, Mo.

[21] Appl. No.: 08/956,774

[22] Filed: Oct. 21, 1997

[51] Int. Cl.$^6$ .................................................. A01N 25/02
[52] U.S. Cl. ........................ 424/405; 424/667; 424/668; 424/669; 424/670; 424/671; 424/672
[58] Field of Search .................................. 424/667–672; 672/405

[56] References Cited

U.S. PATENT DOCUMENTS

| | | | |
|---|---|---|---|
| 97,794 | 12/1869 | Munroe | 424/670 |
| 2,826,532 | 3/1958 | Hosner | 424/672 |
| 2,931,777 | 4/1960 | Shelanski | 252/106 |
| 3,028,299 | 4/1962 | Winicov et al. | 167/17 |
| 3,728,449 | 4/1973 | Hardwick et al. | 424/667 |
| 4,803,008 | 2/1989 | Ciolino et al. | 252/162 |
| 5,002,763 | 3/1991 | Login et al. | 424/80 |
| 5,368,868 | 11/1994 | Winicov | 424/667 |
| 5,635,492 | 6/1997 | Corby | 514/54 |
| 5,643,608 | 7/1997 | McKinzie et al. | 424/667 |

OTHER PUBLICATIONS

Milks et al: Iodine pp. 472–484 Practical Veterinary Pharmacology, 1949.

*Primary Examiner*—Neil S. Levy
*Attorney, Agent, or Firm*—Hovey, Williams, Timmons & Collins

[57] ABSTRACT

Stable, aqueous, iodine-based germicidal compositions are provided which include respective amounts of available iodine, non-ionic surfactant (e.g., polyoxyethylene, polyoxypropylene block copolymers) and an iodine-solubilizing halide ion selected from the group consisting of $Cl^-$ and $Br^-$ and mixtures thereof. Use of $Cl^-$ and/or $B^-$ substantially reduces or completely eliminates the need for iodide ion in the compositions for maintaining available iodine in solution. The compositions can be in the form of dilutable concentrates or final use solutions.

16 Claims, No Drawings

IODINE ANTIMICROBIAL COMPOSITIONS CONTAINING NONIONIC SURFACTANTS AND HALOGEN ANIONS

BACKGROUND OF THE INVENTION

1. Field of the Invention

The present invention is broadly concerned with improved iodine-based aqueous anti-microbial compositions which include respective amounts of available iodine and non-ionic surfactant supplemented with amounts of low cost iodine-solubilizing halide ion selected from the group consisting of chloride and bromide ions and mixtures thereof. More particularly, the invention pertains to such compositions (which may be in the form of dilutable concentrates or final use solutions) which employ Cl$^-$ and/or Br$^-$ ion solubilizing halide ions in combination with non-ionic surfactants so as to sharply reduce or eliminate the need for relatively more expensive iodide ion while at the same time providing stable compositions.

2. Description of the Prior Art

Iodine-based anti-microbial compositions designed for hard surface sanitization or topical application to the skin have long been available. The former type of composition are typically used to sanitize metallic equipment surfaces, e.g., in milk-handling equipment or the like. Topically applied compositions are primarily used in product such as pre-operative antiseptic preparations, hand cleaners and in bovine teat dips for mastitis prevention. See, for example, U.S. Pat. Nos. 3,728,449 and 5,368,868 which describe detergent-iodine products.

U.S. Pat. No. 2,931,777 describes the use of non-ionic surfactants as an aid in improving the solubility of iodine in germicidal preparations. The mixtures described are generally non-aqueous solutions of iodine in a nonionic surfactant which, after preparation, can be added to water to form a use solution. As the iodine is dissolved in the non-ionic surfactant, about 14–55% of the iodine is converted to iodide ions and/or organically bound iodine. Inasmuch as only the molecular form of iodine has germicidal properties, that portion of the originally added iodine converted to iodides or organic complexes adds to the cost of the formulations without giving any germicidal effect. However, the presence of substantial iodide is necessary to keep the active molecular iodine dissolved in the aqueous solution.

U.S. Pat. No. 3,028,299 discloses the concept of adding about 0.25 parts of iodide for each part of iodine to aid in the solubilization of the iodine in solutions containing non-ionic or cationic surfactants. Addition of iodide salts directly to the non-ionic surfactant allows a slight reduction in the amount of iodide otherwise necessary to maintain the molecular iodine dissolved in solution.

U.S. Pat. No. 5,002,763 deals with complexed iodine products, and specifically water soluble complexes of polyvinylpyrrolidone (PVP), hydrogen chloride and iodine. According to the '763 patent, powdered water soluble (PVP)$_2$HCl:I$_2$ complexes result from a two-step preparative process involving first forming an intermediate complex with PVP powder and gaseous HCl followed by the addition of iodine.

SUMMARY OF THE INVENTION

The present invention provides improved iodine-based anti-microbial aqueous compositions in the form of dilutable concentrates or final use solutions which broadly comprise respective amounts of average available iodine and non-ionic surfactant supplemented with a quantity of an iodine-solubilizing halide ion selected from the group consisting of chloride and bromide ions and mixtures thereof. It has been found that such compositions are extremely stable and the need for solubilizing iodide ion therein is greatly reduced or even eliminated. Thus, use can be made of very inexpensive halide ion sources such as sodium chloride or bromide for solubilizing the available iodine in the compositions in lieu of the significantly more expensive iodide ion sources.

The concentrates of the invention generally contain from about 1–30% by weight available iodine and from about 1–30% by weight of non-ionic surfactant. The solubilizing halide ion is normally present therein at a level of from about 0.1–30% by weight. In many instances, such concentrates would also include a minor amount of a buffering agent and other optional ingredients such as emollients, thickeners and wetting agents. The pH of the concentrates would usually be in the range of from about −1 to 8.

A wide variety of non-ionic surfactants can be used in the context of the invention. Generally, the non-ionic surfactants useful in the invention are represented by the formula

R(CHR'—CHR'—O)$_n$—H where R represents the residue of an organic compound containing an active hydrogen or hydroxide and R' represents hydrogen or a C$_1$–C$_4$ alkyl group and n is an integer ranging from about 3–212. The most preferred surfactants are selected from the group consisting of the polyethoxylated polyoxypropylene block copolymers, alkylphenol ethoxylates having C$_4$–C$_{12}$ alkyl groups, ethoxylated fatty alcohols and fatty acids and mixtures thereof. Very good results have been obtained using the Pluronic family of non-ionic surfactants, and especially those having a molecular weight of 2,000 and above.

The selection of a source of solubilizing halide ion is dictated primarily by cost. Normally, such sources are selected from the group consisting of sodium chloride, hydrochloric acid, sodium bromide and hydrobromic acid; if cost is not a prime consideration, then a variety of other halide ion sources can be used.

In some instances, it has been found that the optimum levels of use of chloride and bromide ion may be different. Thus, where chloride ion is used, it is generally present at a level of from about 0.01–5% by weight, more preferably from about 0.01–2% by weight. With bromide ion, the broad range would be from about 0.01–7% by weight, more preferably from about 0.02–5% by weight. Where mixtures of Cl$^-$ and Br$^-$ ions are used, determination of appropriate use levels is a routine matter.

Where skin preparations are desired, use is normally made of one or more emollients, especially those selected from the group consisting of glycerine, propylene glycol, polyethylene glycol, ethylene glycol, polyethoxylated lanolin, sorbitol, and mixtures thereof.

It is also common to include a buffering agent in the iodine compositions of the invention. Buffers such as low molecular weight fatty acids or inorganic acids such as phosphoric acid can be used. Wetting and thickening agents may be added to improve the overall wetting properties and viscosity characteristics of the concentrates and final use solutions. Useful wetting agents include sodium sulfosuccinate dioctylester, whereas thickening agents such as xanthan gum or algin are suitable. For acid sanitizer preparation, 0–50% by weight of an acid source such as phosphoric acid or sulfuric acid can be used. Additional complexing agents such as polyvinylpyrrolidone may be used to supplement the complexing properties of the primary nonionic surfactant.

In the preparation of concentrates in accordance with the invention, the iodine, non-ionic surfactant and iodine-solubilizing halide ion can be added to water and mixed for a sufficient time to create a substantially uniform mixture. As is well known, this causes some of the molecular iodine to be converted to iodide and also results in some iodine complexation. However, the presence of Cl⁻ and/or Br⁻ ions significantly reduces the amount of iodine conversion, thus leaving more of the molecular iodine available as a germicidal agent. For example, 5 g of iodine combined with 95 g of nonylphenol ethoxylate yields, after the iodine dissolves, only 3.6 g of iodine remaining as available iodine. Thereafter, about 28% of the iodine is converted to iodide and/or becomes organically bound. By comparison, a solution in accordance with the present invention was prepared by combining 9 g iodine, 15 g Pluronic P105, 5 g NaCl and 71 g of water; after the iodine was dissolved, 8.37 g iodine remained available. Thus, only 7% of the original iodine was converted to iodide.

It has also been found that the process of dissolving iodine in a non-ionic surfactant solution containing Cl⁻ or Br⁻ ion can be enhanced by the initial addition of a small amount of iodide ion. In the foregoing example, if 7% of the total iodine is added in the form of iodide ion at the beginning of the solubilization process, the mixture will dissolve approximately three times faster than the mixture without added iodide, while retaining the same level of available iodine.

Use solutions in accordance with the invention are most easily prepared by simple dilution of the corresponding concentrates. Alternately, the use solutions can be made directly without intermediate preparation of the concentrates. In the latter case, the preferred process is exactly as that described with reference to the concentrates, i.e., mixing of the use solution ingredients together, preferably in the presence of the appropriate amount of iodide ion.

The concentrates and use solutions of the invention exhibit excellent stability. Specifically, these compositions retain acceptable ranges of available iodine over a room temperature storage period of at least about three months, and more preferably at least about one year. Substantial maintenance of the amount of available iodine refers to the ability of the compositions to maintain the nominal, as-manufactured amount of available iodine within ±20%. Moreover, the solution stability of the compositions is such that the products remain essentially completely homogeneous after extended storage (e.g., at least one week) at temperatures as low as 2° C. and as high as 40° C. Although a given product may separate when frozen, especially after undergoing several freeze-thaw cycles, it should be readily reconstitutable a homogeneous mixture upon simple shaking or mixing.

DETAILED DESCRIPTION OF THE PREFERRED EMBODIMENTS

The following examples set forth preferred methods in accordance with the invention. It is to be understood, however, that these examples are provided by way of illustration only and nothing therein should be taken as a limitation upon the overall scope of the invention.

EXAMPLE 1

Fifteen g of Pluronic P105, 5 g of sodium chloride, 9 g of iodine, and 71 g of deionized water were mixed for four hours at room temperature to yield a concentrated germicidal iodine product. The initial available iodine concentration of this product was 8.4%. After storage for two weeks at 50° C., the available iodine concentration fell to 8.3%.

EXAMPLE 2

A concentrated germicidal iodine product was prepared in a glass reaction vessel by combining 20 g of Pluronic P105, 5 g of sodium chloride, 0.8 g of sodium iodide and 63.2 g of deionized water. The mixture was blended until all of the ingredients dissolved completely. Next, 11 g of iodine was added to the solution and vigorously mixed. The iodine required approximately 24 hours of mixing at room temperature to dissolve. The initial available iodine concentration of the final product was 10.35% by weight. After two weeks at 50° C., the iodine concentration dropped to 10.08% by weight.

EXAMPLE 3

A concentrated germicidal iodine product was prepared in a glass reaction vessel by combining 15 g of Pluronic P105, 10 g of sodium bromide, and 66 g of deionized water. After dissolution of all the ingredients, 9 g of iodine were added. The iodine required approximately 72 hours of mixing at room temperature to dissolve.

EXAMPLE 4

In this example, the concentrated iodine product of Example 2 was used to prepare a ready-to-use germicidal iodine product. First, 4 g of Pluronic P105 was dissolved in 85.8 g of water. Next, 0.2 g of phosphoric acid (a buffer) was mixed with a sufficient amount of NaOH (50%) to adjust the pH to 5.5. 10 g of the concentrated germicidal iodine product of Example 2 was then blended into the mixture.

EXAMPLE 5

In this example, a ready-to-use germicidal iodine solution was prepared without the need for first preparing a concentrate as illustrated in Example 4. 84.74 g of water was blended with 0.06% Keltrol (a thickening agent) to form an intermediate solution. 3 g of Pluronic P105, 0.25 g of citric acid, 0.5 g of sodium chloride, and a sufficient amount of NaOH (50%) (28 g) to adjust the pH to 5.5 were added to the intermediate. 1.07 g of iodine and 0.1 g NaI was then added and the solution mixed vigorously until the iodine dissolved. Finally, 10 g of glycerin emollient was added to yield the final ready-to-use germicidal iodine solution. The initial available iodine concentration was 0.87% by weight, and after two weeks at 50° C., the iodine concentration was 0.866% by weight.

EXAMPLE 6

A ready-to-use germicidal iodine solution was also prepared by combining 0.1 g Keltrol (a thickening agent) and 96.29 g of water to form an intermediate solution. To this intermediate solution was added 0.2% sodium chloride, 1.0% Pluronic P105, 0.05% sodium dioctyl sulfosuccinate, 2% glycerin, 0.1% citric acid, and a sufficient amount of NaOH (50%) to adjust the pH of the mixture to 5.5. 0.11 g of iodine and 0.10% sodium iodate were added, and the pH readjusted to 5.5 with citric acid or NaOH. The initial available iodine concentration of the ready-to-use germicidal iodine solution was 0.090% by weight, and after two weeks at 50° C the iodine concentration was 0.090% by weight.

EXAMPLE 7

A third ready-to-use germicidal iodine solution was prepared by first combining 0.1 g Keltrol and 87.4 g of water.

6.0 g of Pluronic P127 was added and the pH adjusted to 5.5 by adding 0.5 g of citric acid and a sufficient amount of NaOH (50%) to adjust the pH to 5.5. Next, 0.4 g of sodium chloride and 0.60 g of iodine were dissolved in the mixture. Finally, the preparation was completed with the addition of 5 g of glycerin.

EXAMPLE 8

In this example, several solutions containing varying amounts of potassium iodide, sodium chloride, and water were analyzed to determine the solubility of the iodine contained therein. The solubility of the iodine was measured by taking 100 parts of the aqueous test solution, adding an excess of iodine, and mixing until as much iodine as possible is dissolved. Table 1 lists the test solution compositions and the maximum amount of iodine that would dissolve in the respective solutions. The chloride salt alone had little effect on the solubility of iodine in the test aqueous solutions. Sodium chloride in the presence of a nonionic surfactant greatly improved the solubility of iodine because of the synergistic influence of these combined components as shown in the next example.

TABLE 1

Solubility of Iodine in Aqueous Salt Solutions

| Test Solution Composition | Parts of Iodine that Dissolve in 100 Parts of the Test Solution at 25° C. |
|---|---|
| 0% KI 0% NaCl 100% Water | .03 |
| 5% KI 0% NaCl 95% Water | 3.72 |
| 0% KI 5% NaCl 95% Water | .048 |
| 5% KI 5% NaCl 90% Water | 3.58 |

EXAMPLE 9

This example demonstrates the synergistic effect of a combination of Pluronic P105, a polyalkylene oxide block copolymer, with sodium chloride on the solubility of iodine. Several solutions containing varying amounts of Pluronic P105, sodium chloride and water were tested for their ability to solubilize iodine. The solubility of iodine was measured by taking 100 parts of the aqueous test solution containing the nonionic surfactant and the chloride salt and adding iodine in either 0.5 or 1 part increments. After each addition of the iodine dissolved, another increment of iodine was added until the iodine would no longer dissolve. The range listed in Table 2 is the maximum amount of iodine that would dissolve in the particular test solution and the minimum amount of iodine which would exceed the solubility limit.

The data in Table 2 demonstrates the greatly improved solubility of iodine when a polyalkylene oxide block copolymer, such as Pluronic P105, and sodium chloride were combined. For example, a 5% NaCl aqueous solution only dissolved 0.048% iodine, and a 15% Pluronic P105 with no NaCl dissolved 1.5 parts iodine to every 100 parts solution. However, 15% Pluronic P105 with 5% NaCl dissolved 10–11 parts of iodine to every 100 parts of the solution.

Table 2 confirms that there was an optimum concentration of sodium chloride which would dissolve the most iodine. Therefore, the addition of excess sodium chloride to a formulation may not necessarily improve the ability of the solution to dissolve iodine. Addition of excessive amounts of sodium chloride to a nonionic surfactant tended to lower the cloud point of the surfactant. Thus, it was generally better to use a minimum amount of salt for aiding in the solubility of iodine in order to produce a solution that was stable over a wide temperature range.

TABLE 2

Maximum Solubility of Iodine in Pluronic P105/NaCl Mixtures at 25° C.

| Test Solution Composition | Parts of Iodine that Dissolve in 100 Parts of the Test Solution on a w/w Basis |
|---|---|
| 0% NaCl 5% Pluronic P105 95% Water | >2 and <2.5 |
| 0% NaCl 10% Pluronic P105 90% Water | >2 and <2.5 |
| 5% NaCl 10% Pluronic P105 85% Water | >5 and <6 |
| 10% NaCl 10% Pluronic P105 80% Water | >7 and <8 |
| 15% NaCl 10% Pluronic P105 75% Water | >4 and <5 |
| 0% NaCl 15% Pluronic P105 85% Water | >1.0 and <1.5 |

EXAMPLE 10

In this example, the maximum solubility of iodine in Igepal CO720 (a nonylphenol polyethylene oxide) solutions with and without sodium chloride was tested. As indicated in Table 3, the combination of sodium chloride with a nonylphenol polyethylene oxide surfactant dissolved iodine more efficiently than the nonylphenol polyethylene oxide or sodium chloride alone, thereby demonstrating the dramatic synergistic effect of a surfactant and a chloride salt, in combination, on the solubility of iodine in solution. The solubility of iodine was tested in the same manner as described in Example 9 with test solutions comprised of varying amounts of NaCl, Igepal CO720, and water. The results of these tests are listed in Table 3.

TABLE 3

Solubility of Iodine in Igepal Co720/NaCl Mixtures at 25° C.

| Test Solution Composition | Parts of Iodine that Dissolve in 100 Parts of Test Solution on a w/w Basis |
|---|---|
| 0% NaCl 10% Igepal CO720 90% Water | >1.5 and <2.0 |
| 1% NaCl 10% Igepal CO720 89% Water | >2.0 and <2.5 |

EXAMPLE 11

Bromide salts were used in this example to improve the solubility of iodine in aqueous nonionic surfactant solutions. The solubility of iodine was tested in the same manner as described in Example 9. Table 4 demonstrates the influence of sodium bromide on the solubility of iodine in a solution of Pluronic P105. As shown in Table 4, the addition of 5% NaBr to a 15% solution increases the solubility of iodine from 1.0–1.5 parts per 100 parts solution to 11–12 parts per 100 parts solution. Thus, bromide anions were just as efficient as chloride anions at improving the solubility of iodine in a nonionic aqueous solution.

TABLE 4

Improved Solubility of Iodine Using Bromide Salts

| Test Solution Composition | Parts of Iodine that Dissolve in 100 Parts of Test Solution on a w/w Bases |
|---|---|
| 0% NaBr<br>10% Pluronic P105<br>90% Water | 2.3–2.5 |
| 5% NaBr<br>10% Pluronic P105<br>85% Water | 6–8 |
| 10% NaBr<br>10% Pluronic P105<br>80% Water | 2–4 |
| 15% NaBr<br>10% Pluronic P105<br>75% Water | 2–4 |
| 0% NaBr<br>15% Pluronic P105<br>85% Water | 1.0–1.5 |
| 5% NaBr<br>15% Pluronic P105<br>80% Water | 11–12 |
| 10% NaBr<br>15% Pluronic P105<br>75% Water | 9–10 |
| 15% NaBr<br>15% Pluronic P105<br>70% Water | 7–8 |

EXAMPLE 12

In this example, the process of dissolving iodine in a nonionic surfactant solution which contains chloride or bromide anions was facilitated by the addition of a small amount of iodide anions. As was the case of the 15% Pluronic P105 solution with 5% sodium chloride, approximately 7% of the iodine that dissolved reacted to form iodide ions. Therefore, 7% of the total iodine was added in the form of iodide at the beginning of the solubilization process. A solution of 15% Pluronic P105, 5% sodium chloride, and 0.74 g of sodium iodide dissolved 8.37 parts of iodine three times faster than a solution that contained no iodide initially, and most of the iodine that dissolved remained in the form of available iodine. Table 5 demonstrates the difference in time required to dissolve iodine with and without a small amount of sodium iodide.

TABLE 5

Influence of Iodide Salts on the Rate of Solution of Iodine

| Test Solution Composition | Time Required to Dissolve Iodine |
|---|---|
| 15% Pluronic P105<br>5% NaCl<br>9% Iodine<br>0% NaI<br>71% Water | 80 hours |
| 15% Pluronic P105<br>5% NaCl<br>9% Iodine<br>0.79% NaI<br>70.21% Water | 24 hours |

EXAMPLE 13

In addition to the use of sodium chloride, other chloride substances were used effectively to solubilize iodine in solution. Table 6 demonstrates the effect of potassium chloride, lithium chloride, and hydrochloride acid on the solubility of iodine in a 15% Pluronic P105 solution. The solubility of iodine was tested in the same manner as described in Example 9.

TABLE 6

Influence of Different Chloride Substances on the Solubility of Iodine

| Test Solution Composition | Parts of Iodide that Dissolve in 100 Parts of Solution |
|---|---|
| 15% Pluronic P105<br>80% Water<br>5% HCL | 13–14 |
| 15% Pluronic P105<br>80% Water<br>5% LiCl | 2–3 |
| 15% Pluronic P105<br>80% Water<br>5% KCL | 1–2 |

EXAMPLE 14

In this example, the free iodine concentration of several aqueous solutions was determined. The data listed in Table 7 indicates that an increase in the concentration of chloride or iodide had the effect of lowering the free iodine value of the solution because chloride and iodide will complex with iodine in the presence of a nonionic surfactant. As shown in Table 7, the free iodine values for the test solutions containing chloride were significantly higher than the corresponding solutions containing an equivalent amount of iodide. A high free iodine value usually corresponds to a more effective germicidal agent. It is often desirable to optimize the free iodine concentration so the level is high enough for antimicrobial effectiveness but not so high that it causes corrosion. The free iodine level can be optimized by using a mixture of chloride/bromide and iodide to complex the iodine.

TABLE 7

Free Iodine Values for Solutions Containing Chloride or Iodide

| Test Solution Composition | Free Iodine Value |
|---|---|
| 15% Pluronic P105<br>3% NaCl<br>2% Iodine<br>80% Water | 40 ppm |
| 15% Pluronic P105<br>6% NaCl<br>2% Iodine<br>78.5% Water | 24 ppm |
| 15% Pluronic P105<br>1.5% NaI<br>2% Iodine<br>80% Water | 0.7 ppm |
| 15% Pluronic P105<br>3% NaI<br>2% Iodine<br>80% Water | 0.06 ppm |
| 3% Pluronic P105<br>1% NaCl<br>1% Iodine<br>95% Water | 184 ppm |
| 3% Pluronic P105<br>2% NaCl | 92 ppm |

TABLE 7-continued

Free Iodine Values for Solutions Containing Chloride or Iodide

| Test Solution Composition | Free Iodine Value |
|---|---|
| 1% Iodine<br>94% Water<br>3% Pluronic P105<br>0.5% Sodium Iodide | 7 ppm |
| 1% Iodine<br>95.5% Water<br>3% Pluronic P105<br>1% Sodium Iodide | 4 ppm |
| 1.0% Iodine<br>95% Water | |

EXAMPLE 15

The long term stability of iodine can be improved by the addition of an oxidant such as iodate to the formula. U.S. Pat. No. 4,271,149 describes the improved stability that can be obtained when an oxidant is added to a system that contains iodine and iodide species. Similar stability is obtained when iodate is added to a formula that contains iodine and chloride. Table 8 shows the iodine stability of a formulation with and without the addition of iodate.

TABLE 8

Iodine Formulations Containing Chloride and Iodate

| Formula | Initial Available Iodine | Available Iodine After Four Weeks at 50° C. |
|---|---|---|
| 2% Pluronic P105<br>0.5% Iodine<br>0.3% NaCl<br>97.2% Water | 0.45% | 0.36% |
| 2% Pluronic P105<br>0.5% Iodine<br>0.3% NaCl<br>0.1% NaIO3<br>97.1% Water | 0.45% | 0.42% |

The following table summarizes the approximate broad, preferred and most preferred ranges of essential and optional ingredients for the concentrates and use solutions in accordance with the invention.

TABLE 9

| Ingredient/Property | Broad Range (% by wt.) | Preferred Range (% by wt.) | Most Preferred Range (% by wt.) |
|---|---|---|---|
| Concentrates | | | |
| Acid Source | 0–50% | 0–42% | 0–42% |
| Iodine | 1–30 | 2–20 | 8–12 |
| Iodine-Solubilizing Halide Ions | 0.1–30 | 0.1–12 (Cl$^-$)<br>0.5–25 (Br$^-$) | 1.8–3 (Cl$^-$)<br>4–7 (Br$^-$) |
| Non-Ionic Surfactant | 1–30 | 5–25 | 15–20 |
| Iodide Ion | .01–20 | .05–10 | .1–5 |
| Emollient | 0–20 | 1–10 | 2–8 |
| Buffering Agent | 0–2 | 0.1–1 | 0.2–0.7 |
| Polyvinylpyrrolidone | 0–15 | 0–12.5 | 0–10 |
| Water | q.s. | q.s. | q.s. |
| Viscosity | 1–5000 cps | 1–2000 cps | 1–1000 cps |
| pH | –1 to 8 | –1 to 7 | –1 to 5 |
| Use Solutions | | | |
| Iodine | .05–5 | .05–2 | .05–1 |
| Iodine-Solubilizing | 0.01–10 | 0.01–5 (Cl$^-$) | 0.01–2 (Cl$^-$) |
| Halide Ions | | 0.01–7 (Br$^-$) | 0.02–5 (Br$^-$) |
| Non-Ionic Surfactant | 0.01–10 | 0.02–7 | 0.2–5 |
| Iodide Ion | .01–5 | .01–3 | .01–.5 |
| Emollient | 0–15 | 0–10 | 0–10 |
| Polyvinylpyrrolidone | 0–5 | 0–3.5 | 0–2.5 |
| Water | q.s. | q.s. | q.s. |

We claim:

1. An aqueous antimicrobial composition comprising:
   an amount up to about 12% by weight of available iodine including molecular iodine;
   an amount of up to about 30% by weight of non-ionic surfactant having the formula R(CHR'—CHR'—O)—H, where R represents the residue of an organic compound containing an active hydrogen or hydroxide and R' represents hydrogen or a $C_1$–$C_4$ alkyl group and n is an integer ranging from about 3–212; and
   a quantity of halide ion selected from the group consisting of chloride: and bromide ions and mixtures thereof the ratio of said halide ion to said available iodine being from about 0.22:1 to 3.8:1. said available iodine; non-ionic surfactant and halide ion being present in said aqueous composition.
   said composition having a pH of from about –1 to 7.

2. The composition of claim 1, said composition being a dilutable concentrate.

3. The composition of claim 1, said composition being a use solution.

4. The composition of claim 1, said non-ionic surfactant being present at a level of from about 1–30% by weight.

5. The composition of claim 4, said level being from about 5–25% by weight.

6. The composition of claim 1, said halide ion being present at a level of from about 0.1–30% by weight.

7. The composition of claim 6, said halide ion being chloride ion and being present at a level of from about 0.1–12% by weight.

8. The composition of claim 6, said halide ion being bromide ion and being present at a level of from about 0.5–25% by weight.

9. The composition of claim 1, including an acid source.

10. The composition of claim 1, including an amount of polyvinylpyrrolidone.

11. The composition of claim 1, including a buffering agent.

12. The composition of claim 1, including an amount of an emollient.

13. The composition of claim 1, said halide ion being derived from a source selected from the group consisting of sodium chloride, hydrochloric acid, sodium bromide and hydrobromic acid.

14. The composition of claim 1, including an amount of iodide ion.

15. The composition of claim 14, said iodide ion being present at a level of from about 0.01–20% by weight.

16. The composition of claim 1, aid non-ionic surfactant being selected from the group consisting of the polyethoxylated polyoxypropylene block copolymers, alkylphenol ethoxylates having $C_4$–$C_{12}$ alkyl groups, ethoxylated fatty alcohols and fatty acids and mixtures thereof.

* * * * *

UNITED STATES PATENT AND TRADEMARK OFFICE
CERTIFICATE OF CORRECTION

PATENT NO. : 5,916,581
DATED : June 29, 1999
INVENTOR(S) : Foret, Chris and Hemling, Thomas C.

It is certified that error appears in the above-identified patent and that said Letters Patent is hereby corrected as shown below:

Column 10,
Line 18, please insert a subscript -- n -- after the ")".

Signed and Sealed this

Twelfth Day of March, 2002

Attest:

Attesting Officer

JAMES E. ROGAN
Director of the United States Patent and Trademark Office